United States Patent [19]

Sealfon

[11] Patent Number: 5,261,882

[45] Date of Patent: Nov. 16, 1993

[54] NEGATOR SPRING-POWERED SYRINGE

[76] Inventor: Andrew I. Sealfon, 17 Industrial Pl., Middletown, N.Y. 10940

[21] Appl. No.: 53,873

[22] Filed: Apr. 26, 1993

[51] Int. Cl.$^5$ ............................................. A61M 37/00
[52] U.S. Cl. .................... 604/135; 604/246; 128/DIG. 12
[58] Field of Search ............... 604/135, 134, 133, 132, 604/131, 151–154, 121, 246, 51, 218; 128/DIG. 12

[56] References Cited

U.S. PATENT DOCUMENTS

| | | | |
|---|---|---|---|
| 4,298,000 | 11/1981 | Thill et al. | 604/135 |
| 4,300,554 | 11/1981 | Hessberg et al. | 604/135 |
| 4,313,439 | 2/1982 | Babb et al. | 604/135 |
| 4,755,172 | 7/1988 | Baldwin | 604/131 |
| 4,997,420 | 3/1991 | LeFevre | 604/131 |

Primary Examiner—J. Yasko

[57] ABSTRACT

A negator spring-powered I.V. pump of compact size resulting from imparting a non-circular, rather than a linear configuration to the negator spring; the non-circular configuration taking up less size or linear dimension which, added to the linear dimension of the syringe of the pump, results in an optimum reduced overall pump size that is convenient for portable ambulatory I.V. therapy.

4 Claims, 4 Drawing Sheets

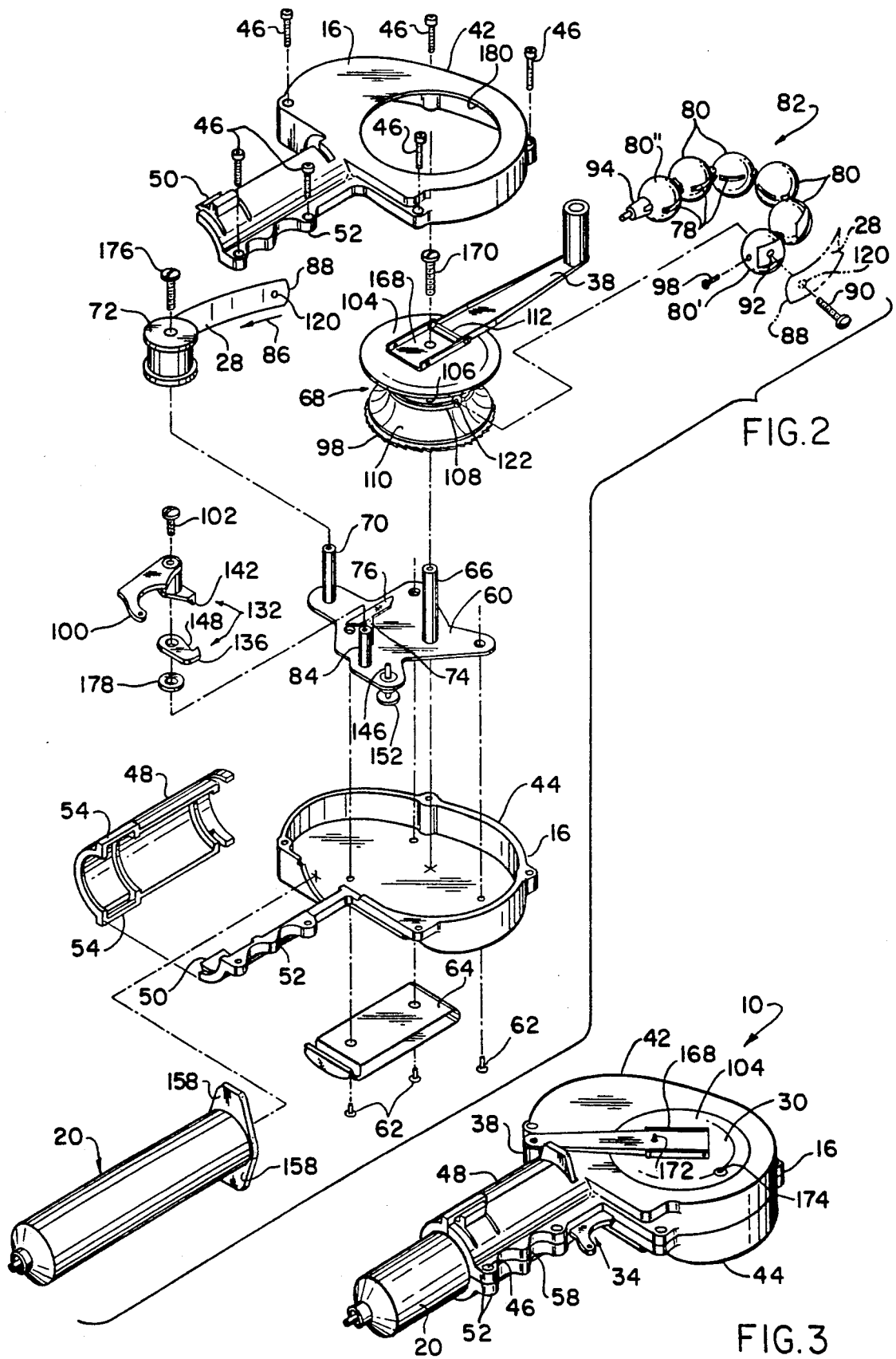

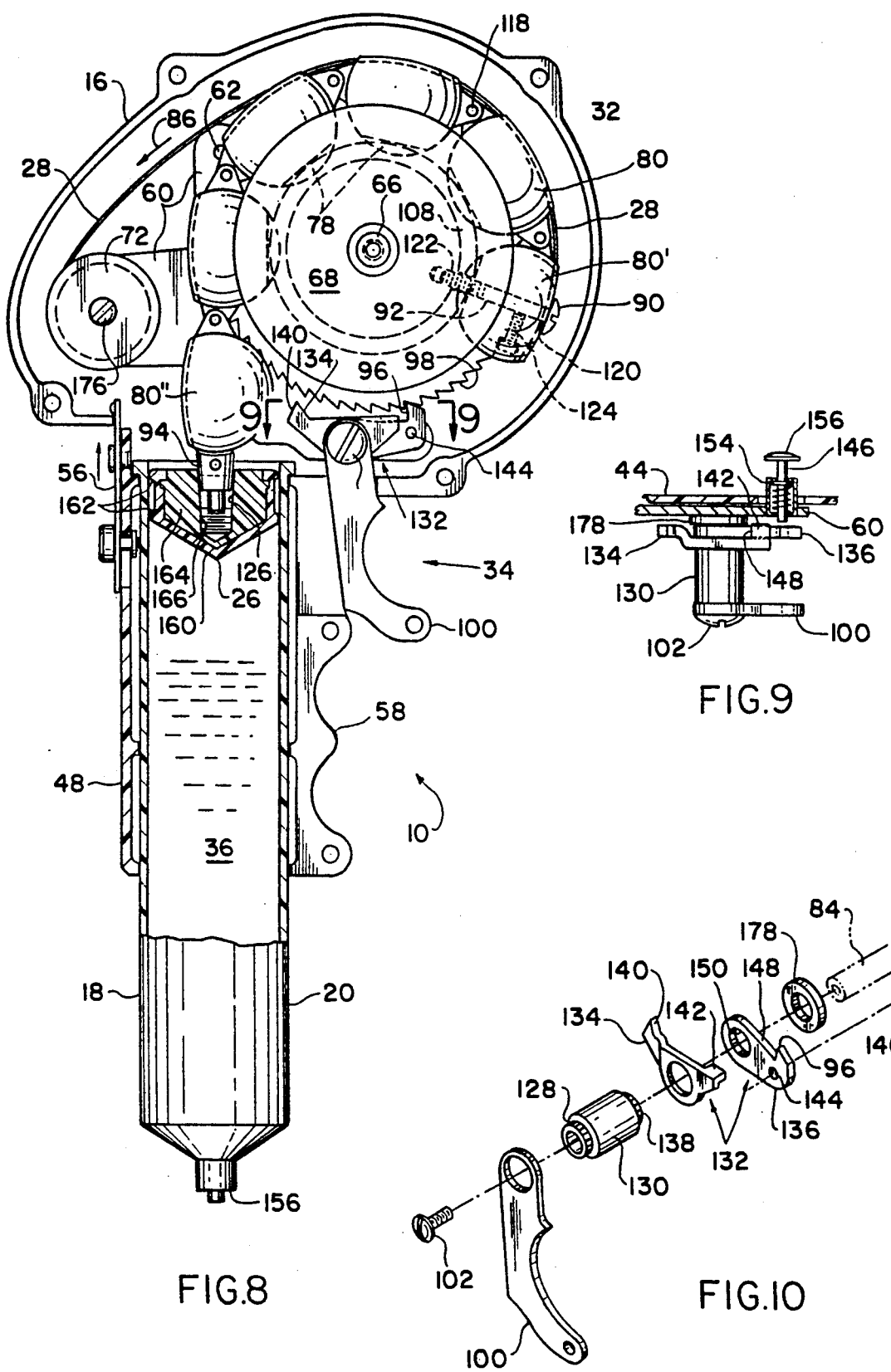

NEGATOR SPRING-POWERED SYRINGE

The present invention relates generally to improvements for a portable non-electric intravenous (I.V.) pump specifically intended for portable ambulatory therapy at an optimum low cost, and more particularly to an improved I.V. pump which in practice contributes to providing intravenous therapy without a patient being "lassoed" to a hospital bed or having to wheel an I.V. pole in a hospital or at home. The within inventive I.V. pump allows a patient who is otherwise able to walk, to receive therapy outside of the hospital with an effective, low cost I.V. System.

As will be better appreciated as the description proceeds, the within inventive I.V. pump is, construction-wise and by its operating mode, low enough in cost to be classified as a reusable/disposable article of manufacture that the patient is able to refill as an intravenous fluid source as often as needed, but may be disposed of when the course of treatment is over.

Underlying the present invention is the recognition that facilitated use for ambulatory I.V. therapy, and also contributing to low cost, as well to attain other significant advantages and benefits, requires an optimum compact size in the I.V. pump. That is, the pump which has as an essential component a linear syringe barrel, also according to prior art practice usually also utilizes a correspondingly linear piston rod, such that in the ready position of the piston rod, i.e. when the piston rod is at the start of its power stroke lengthwise of the syringe barrel, the size of the I.V. pump is the linear size of the syringe barrel and also the linear size of the piston rod. It is only after the piston rod completes its power stroke lengthwise of the syringe barrel that the size of the I.V. pump is reduced to the size of the syringe barrel.

In contrast to the aforesaid, the within inventive I.V. pump, which is powered in operation by a negator spring, has a significantly reduced overall size consisting of the unavoidable linear dimension of the syringe barrel, but a non-linear dimension of the negator-powered piston rod, said latter non-linear dimension being approximately half the linear dimension that would have been dictated had the prior art practice of matching the size of the piston rod to the size of the syringe barrel been followed.

EXAMPLES OF THE PRIOR ART

Heretofore, syringes have been powered by springs, one such syringe being illustrated and described in Babb et al. U.S. Pat. No. 4,313,439 issued on Feb. 2, 1982 entitled "Automated, Spring-Powered Medicant Infusion System". The size of the patented syringe is the linear dimension of the syringe barrel 12, the approximate same linear dimension of the piston rod 14, and the additional linear dimension of the curved path of the spring-powered spheres 18, thus resulting in no reduction in the overall size or compact condition of the Babb et al. I.V. pump.

In Thill et al. U.S. Pat. No. 4,202,333 issued on May 13, 1980 for "Fluid Dispensing Device", use is specifically made of a negator spring 30 to urge the piston rod 18 through its power stroke axially of the syringe barrel 14, but in the ready position of the piston rod 18 at which the negator spring is at a corresponding ready position to the right of the partway position of movement depicted in FIG. 2, the overall size of Thill et al. I.V. pump is again the combined linear sizes of the syringe barrel 14 and the piston rod 18, thus again failing to contribute to the reduction in overall size or compact condition of the I.V. pump.

Broadly, it is an object of the present invention to provide a negator spring-powered I.V. pump overcoming the foregoing and other shortcomings of the prior art. More particularly, using to advantage the powering of the piston rod with a negator spring which can, because of its resiliency, be configured in a non-linear shape, the within inventive I.V. pump also uses a piston rod that similarly has an operative non-linear shape, so that there is a significant reduction in the overall size and compactness of the I.V. pump.

The description of the invention which follows, together with the accompanying drawings should not be construed as limiting the invention to the example shown and described, because those skilled in the art to which this invention appertains will be able to devise other forms thereof within the ambit of the appended claims.

FIG. 2 is an exploded perspective view of the syringe best illustrating the individual components and sub-assembly of components thereof;

FIG. 3 is a view from the same perspective as FIG. 2, but illustrating the syringe in an assembled condition ready for use;

FIG. 8 is a right side elevational view of the syringe with the housing cover thereof and other components removed to better illustrate the assembly of the internal components thereof;

FIG. 9 is a sectional view taken along line 9—9 of FIG. 8 illustrating a latching mechanism of the syringe;

FIG. 10 is an exploded perspective view of the trigger mechanism sub-assembly of the within syringe;

Figure 1:
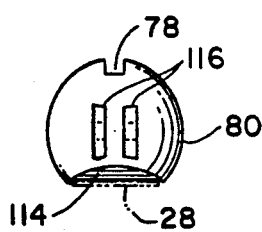
FIG. 1 is a partial perspective view showing a typical use of the within inventive syringe on the belt of a patient and delivering medicant intravenously to the patient.

FIG. 1 illustrates the use of the within inventive syringe, generally designated 10, as an intravenous pump for a patient 12. As such, the syringe or pump 10 is supported on a belt 14 and includes a housing 16 for the cylindrical barrel 18 of a syringe 20 connected via a catheter 22 terminating in a needle 24 appropriately connected to the patient 12 for well understood intravenous service. To drive the piston head 26 of the syringe 20 through a power stroke, use is made of a negator spring 28 through a path of movement 30 that is characterized by a circular shape as illustrated in FIG. 1. That is, although the syringe barrel 18 is essentially linear or axial, as shown, the negator spring-powering means 28 for the syringe 20 is characterized by not being linear, but by being non-linear and, more particularly, by being circular and thus assuming, when not in use, the circular shape 30. This is in contrast to currently known syringes in which the syringe is similarly linear and so also is the piston rod or piston-powering means for these known or prior art syringes, so that the total size of the syringe is necessarily the two linear dimensions of the syringe per se and the storage compartment for the syringe-powering means. In the within inventive syringe, however, and as will be explained in greater detail subsequently, the overall size of the negator-powered syringe or IV pump 10 is significantly more compact, consisting of the linear dimension of the syringe barrel 18, but a non-linear shaped storage compartment 32 for the piston-powering means, wherein said non-linear shaped storage compartment contributes to a significant reduction in size. Thus, and again as will be better understood as the description proceeds, the piston-powering means, namely the negator spring, is initially in a circular configuration denoted by the reference numeral 28 and, when released by actuating a trigger mechanism 34, urges a piston head 26 operating within the syringe 20 through a power stroke to cause the delivery of medicant 36 to the patient 12. When all medicant 36 has been dispensed by the syringe 20, the negator spring 28 is cranked by use of a crank 38 back into its unwound condition preparatory to again urging the syringe piston head 26 through a power stroke. In lieu of a mechanical uncoiling of the negator spring using crank 38, use can also be made of a battery-powered mechanism 40 to achieve the same function (see FIG. 12).

Figure 4:
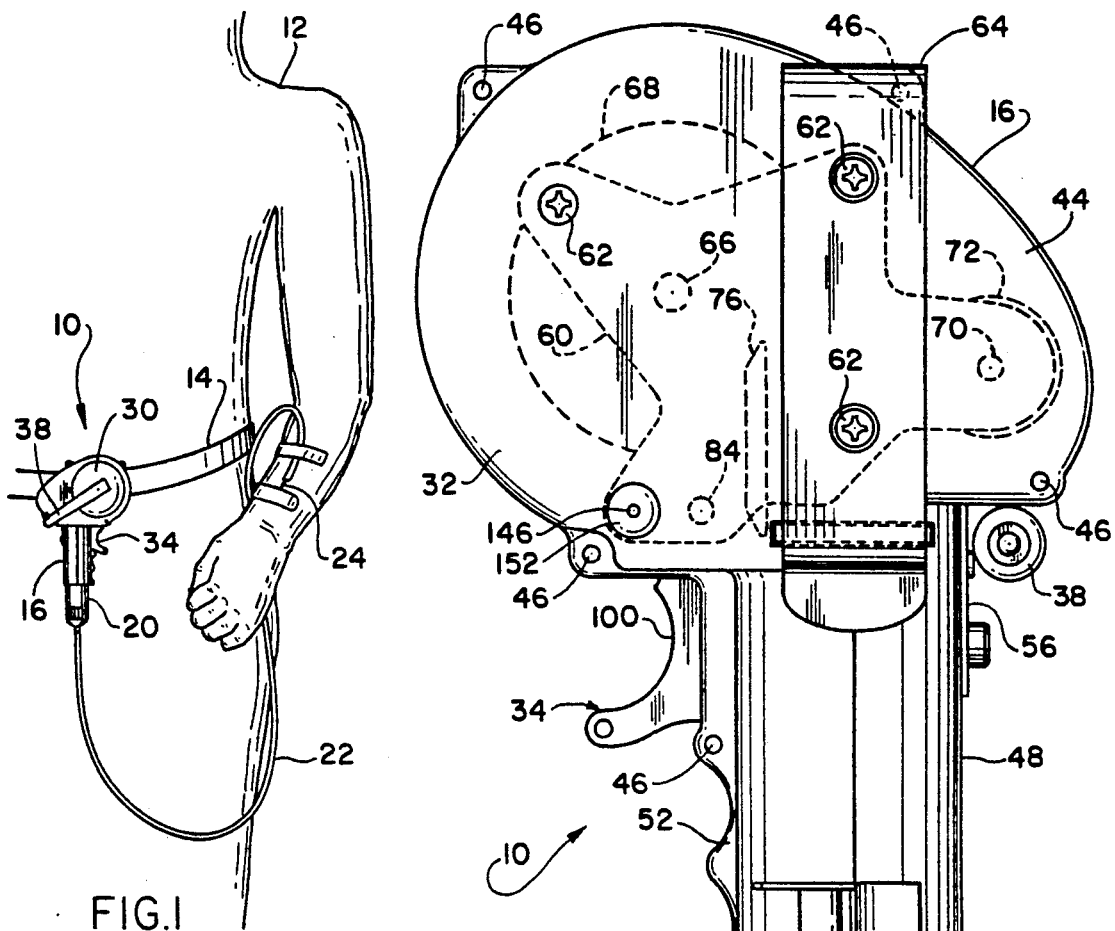
FIG. 4 is an enlarged scale left side elevational view of the syringe.

As best illustrated in FIGS. 2 and 3, housing 16 for the syringe barrel 20 is comprised of two halves 42 and 44 preferably of plastic construction material and assembled to each other using screws 46. Cooperating cylindrical cover portions 48 of the housing halves 42 and 44 receive spring hooks 50 on finger grip configurations 52 in spring-receiving openings 54. The cooperating cover 48 also has a latch member 56, as best shown in FIG. 8, to facilitate the engagement in place of the syringe barrel 20. When in use, cover 48 cooperating with its counterpart, housing section 52, serves as a convenient cylindrical pistol grip 58 in addition to holding syringe barrel 20 in an operative position to use the urgency of the negator spring for a power stroke of the piston head operating within the syringe barrel 18. An internal component-positioning plate 60 is mounted within housing half 44 using three screws 62. Externally of the housing half 44 a clip 64 for the patient's belt 14 is attached by two of the three screws 62, as illustrated in FIG. 4.

The components disposed in their proper place in the compartment 32 by the cooperating housing portion 16 of the two halves 42 and 44 includes an axle member 66 establishing a rotating axis for a spindle assembly, generally designated 68, and a similarly functioning axle 70 for a spool 72 which, in a well understood manner, supports the helical coils of a negator spring 28, the spindle 68 and the negator spring 28 being the major components of the spring urgency or driving force previously noted by the reference numeral 30 in the general description provided in conjunction with FIG. 1. Plate 60 has a projection 74 which supports a guide vane 76 that projects into a cooperating groove 78 in link-like spheres 80 of an interconnected arrangement of similarly constructed spheres 80 which form, in their assembled interconnected condition, a piston rod 82 for the syringe 20. That is, while the syringe 20 has, as best illustrated in FIG. 8, a piston head 26, the spheres 80, one of which is shown in isolated perspective in FIG. 5, is more meaningfully the piston rod for the piston head 26 and is what urges the piston head 26 from its initial position of movement as illustrated in FIG. 8 through a power stroke along the axial length of the syringe barrel 18 and in the process expelling the medicant 36 from the syringe chamber.

Still referring to plate 60, it will be noted that it additionally includes an axle 84 serving as a rotation axis for a trigger mechanism, generally designated 34, which functionally releases the urgency of the negator spring 28 when the trigger mechanism 34 is depressed and the structure which holds the helical coils 28 in their uncoiled, extended condition, when latched, is unlatched by the trigger mechanism 34.

Figures 5, 6, 7:
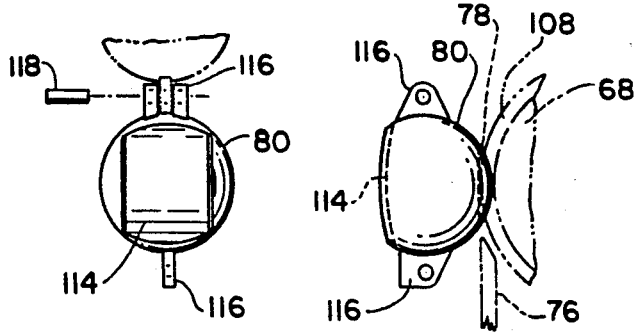
FIG. 5 is an isolated top view of a sphere serving in combination with similar interconnected spheres as the piston rod for the within inventive syringe.
FIG. 6 is a front view of the FIG. 5 sphere in full line perspective illustrating the manner of its connection with another cooperating sphere shown in phantom perspective.
FIG. 7 is a side elevational view of a sphere as exemplified by that shown in FIG. 5 further illustrating the manner in which the sphere tracks as part of a piston rod when providing a power stroke for the within inventive syringe.

The drive or piston rod generally designated 30 is made up of a sub-assembly consisting of the negator spring 28, its support spool 72, the spindle assembly 68, and the interconnected plural spheres 82, best illustrated in FIG. 2 said plural spheres 82 consisting of the individually designated sphere 80 of FIGS. 5-7. Functioning in a well-understood manner, negator spring 28, when uncoiled from its normal helically coiled condition about spool 72, exhibits a uniform urgency to return to its helically coiled condition and this phenomenon is used in a well understood manner to impart a constant pulling force as noted by the arrow 86 in FIG. 2 for the extended uncoiled length 88 of the negator spring 28. Thus, as is well understood, and as is illustrated in FIG. 2, negator spring 28 is adapted to be uncoiled from spool 72 and extended from location 70 in encircling relation about the circular configuration 82 consisting of the individual spheres 80 in which, as shown in phantom prospective in FIG. 2, the negator spring end 88 is connected by screw 90 into a threaded opening 92 in a distal located sphere 80' of the interconnected chain 82. At this point it should be noted that a proximal located sphere 80'', namely the sphere at the opposite end of the chain 82 and adjacent to a stud fitting 94 is then adjacent to the piston head 26 and thus at the opening into the syringe barrel 18. In this condition it is apt to characterize the IV pump 10 as being in a ready condition preparatory to use. In this ready condition, as best understood from FIG. 8, the spindle 68 is prevented from rotating by the latching of a pawl 96 in a tooth of a ratchet wheel 98 of the spindle 68. However, when trigger 100 is depressed causing rotation of the pawl 96 about the axis of the trigger-attaching screw 102, the ratchet wheel 78 is released and the urgency produced by the negator spring 28 in returning to its helically coiled condition about the spool 72 results in the interconnected spheres 82, attached much like a piston rod to the piston head 26, in effectively urging the piston head 26 through a power stroke along the axial length of the syringe barrel 18. At this point in the description it is significant to note that because the interconnected spheres 82, (as clearly shown in FIGS. 2 and 8) are in a circular configuration, rather than a linear configuration, the size that must be allotted for the axial stroke through the syringe piston 22 for both travel of the piston head 26 and also for the means powering the piston head 26 in movement are not a total of two linear dimensions, but rather the total of only one linear dimension, namely the linear dimension of the syringe barrel 18, and the significantly reduced dimension, because it is non-linear, of the circular arrangement of the interconnected spheres 82.

The spindle, generally designated 68, about which the flexible piston rod or interconnected spheres 82 track, is an assemblage of a face plate 104, a conical wall 106, a center rim 108, a combination opposing conical wall 110 and ratchet wheel 98, all of which are bolted together by transversely disposed screws (not shown). Appropriately mounted on the exterior of face plate 104 is handle 38 foldable about an axis 112 between the two positions illustrated in full line and phantom perspective in FIG. 12.

Referring to details now of the flexible piston rod or interconnected chain of spheres 82, reference should be made to FIGS. 5, 6 and 7 which show details of the individual sphere 80 comprising the chain 82. More particularly, as shown in the figures referred to, each sphere 80 will be understood to have a contoured outer surface 114 serving as a seat for the negator spring 28, as shown in phantom perspective in FIG. 5. On the side opposite, each sphere 80 has a guide groove 78 which, during tracking of the assembled spheres 82 about spindle 68 receives in a projected relation a rim 108 of the spindle, as best illustrated in FIG. 8. To complete their interconnection, each sphere 80 has appropriate cooperating male and female bosses 116 joined by connecting pins 118, as shown in FIG. 6 and FIG. 7. As best illustrated in FIG. 8, the distal located sphere 80, i.e. the one at the end of the interconnected link 82, herein designated 82', is provided with a through hole 92 to receive screw 90 projected through a hole 120 in the negator spring end 88. Screw 90 is threadably tightened in the tapped hole 127 of rim 108 of the spindle assembly 68 and held by a set screw 124. At the opposite end of the linkage 82, namely in the proximal located sphere herein designated 88", a location which advantageously locates sphere 80" at the opening into the syringe 20, use is made of a stud fitting 94 extending from the sphere 80" and establishing engagement in a tapered hole 126 of piston head 26 shown in its ready position in FIG. 8 within the syringe barrel 18.

A trigger mechanism, generally designated 34, is provided to hold the negator spring 28 in its uncoiled condition preparatory to release and the negator spring 28 then assuming its helically coiled position about its support spool 72. The referred-to trigger mechanism is best understood from FIGS. 8, 9 and 10. In addition to release of the negator spring, another function of the control trigger mechanism 34 is also to allow the user of the IV pump 10 to pulse the trigger 100 in a single cycle which dispenses 1 ml. of medication.

A preferred construction and operating mode for the trigger mechanism 34 includes the structural elements shown in exploded perspective in FIG. 10. As shown therein, trigger 100 is fixedly attached in a shoulder 128 of a hollow shaft 130. In the continuous flow mode of operation, ratchet pawl 132 comprised of the two parts 134 and 136, is seated in an opposite shoulder 138 of the shaft 130. The pawl piece 134 has a hook 146 on one end, and a shaped configuration 142 at its opposite end, the latter adapted to seat relative to a release hook 96 in the other pawl part 136, which pawl part has an opening 144 to receive a detent pin 146. In the assembly of the pawl parts 134 and 136 a spring, not shown, urges the shaped configuration 142 against the surface 148 and, thus, behind the release hook 96. A through bore 150 in part 136 is sized to permit free rotation of part 136 about shaft 84 along with the hollow shaft 130. In the assembly of the pawl 132, both parts 134 and 136 are biased counterclockwise, as viewed in FIG. 8, by an appropriate torque spring (not shown). Trigger 100 being connected as it is through shaft 130 to part 134 in an offset bell-crank fashion is accordingly also biased in a counterclockwise direction.

Detent pin 146, shown in phantom perspective in FIG. 10 and in full line perspective in FIG. 2, is an assembled component of plate 60 as well as of the control trigger mechanism 34. Pin 146 has a grip knob 152 and is spring biased outwardly within its housing 154, as shown in FIG. 9. To initiate the continuous flow mode of operation, pin 146 is depressed and the resulting descending movement projects pin 146 into opening 144 in pawl part 136 and thereby prevents release hook 96 from engaging teeth on ratchet wheel 98.

The hypodermic syringe 20 used for the storage of intravenous fluid 36, as best shown in FIG. 8, includes a barrel 18 of a conventional cylindrical shape, a coupling 156 outlet for receiving in attached relation a catheter tube 22 terminating in a hypodermic needle 24 (see FIG. 1). Completing the construction of the barrel 18 is a finger grip or laterally extending flanges 158. The syringe that is preferred for use is one having a 60 ml. capacity barrel, although it will be understood that an increased size in the IV pump 10 will also be able to accommodate a correspondingly increased capacity barrel.

As generally understood, the power stroke of syringe 20 contemplates that piston head 26 will be urged through movement axially of the barrel 18 or, in other words, a movement from the first position of movement shown in FIG. 8 to one in which the piston head descends to the position of movement in which it is adjacent the outlet 156. For completeness sake it is to be noted that piston head 26 has an outer member 160 that is contoured with annular seals 162 or, optionally, can be adapted to incorporate O-ring seal members (not shown). Within member 160 there is provided a second core-like member 164 having threads 166 at the base of a tapered bore 126. The projection or extension 94 of the proximal located sphere 80" is projected into and appropriately secured within the hole 126. After the syringe 20 is filled to the capacity desired, the barrel outlet 156 is protected against leakage by a seal cap (not shown) preparatory to use of the syringe. To facilitate handling of the IV pump 10, finger grips 58 which cooperate with the trigger 100 are attached to the barrel housing 16, as shown in FIG. 8, in any appropriate manner.

The description which now follows is of the preferred manner of assembling the intravenous device 10. This assembly contemplates that plate 60 and belt clip 64 be secured to the housing half 44 by screws 62. Next, spindle assembly 68 is readily slipped over shaft 66 on plate 60. Plate 168 of crank member 38 is then secured in place by a screw 170 threadably engaged in the threaded bore of shaft 66. It is to be noted that the components are dimensioned or sized so that both spindle assembly 68 and plate 168 are free wheeling about shaft 66. It is also to be noted that a pin 172 on crank 38 is sized to engage a grip hole 174 in face plate 104 when arm 38 is in its unfolded condition as shown in phantom perspective in FIGS. 11 and 12.

The next recommended step in the assembly of the intravenous pump 10 is to place the flexible piston rod formed by the interconnected spheres 82 in an initial position of movement so that through bore 92 in the distal sphere 80' aligns with the tapped or threaded hole 122 in rim 108. Spring 28 with core spool 72 is then placed over shaft 70 and secured in place with screw 176. Here also, it is to be noted that the components are appropriately dimensioned or sized so that core spool 72 is free to rotate about shaft 70. The negator spring end 88 is now uncoiled and extended to a location where screw 90 can be passed through hole 120 in the spring 28 and aligned with hole 92 in sphere 80', and then secured in place using the threaded or tapped hole 122 of rim 108 wherein the screw 90 which achieves this is further held in place using set screw 124, as shown in FIG. 8. From this initial positioning of the interconnected spheres 82 it is in a ready position from which it is urged through movement in tracking relation about the spindle 68 under the urgency of the negator spring 28 as it helically coils about the support spool 72, said movement of the interconnected spheres 82 being in a counterclockwise direction.

The next recommended step in the assembly of the intravenous pump 10 is the assembly of the control trigger mechanism 34. This is achieved by using trigger axle 84 to receive the components shown in exploded perspective in FIG. 10, and the maintaining of these assembled components using screw 102 which threadably engages in the threaded bore of axle 84. At this point in the assembly, a washer 178 and pawl part 134 will be understood to have been previously placed on shaft 84 so that the extension 142 on pawl part 134 is spring biased against surface 148 and pawl part 134, as a consequence of which pawl 132 is positioned so that the release hook 96 thereon engages a cooperating tooth of the teeth arranged circumferentially about the ratchet wheel 98.

The final assembly step contemplates that the right housing half 42 be connected to the other housing half 44 using screws 46, care being taken to manipulate crank 38 through the face plate opening 180 in the housing half 42. Cover member 48 is then placed in covering relation over the upper portion of the syringe 20 as a result of the engagement of spring hooks 50 in cooperating recesses 54.

Figures 11, 12:
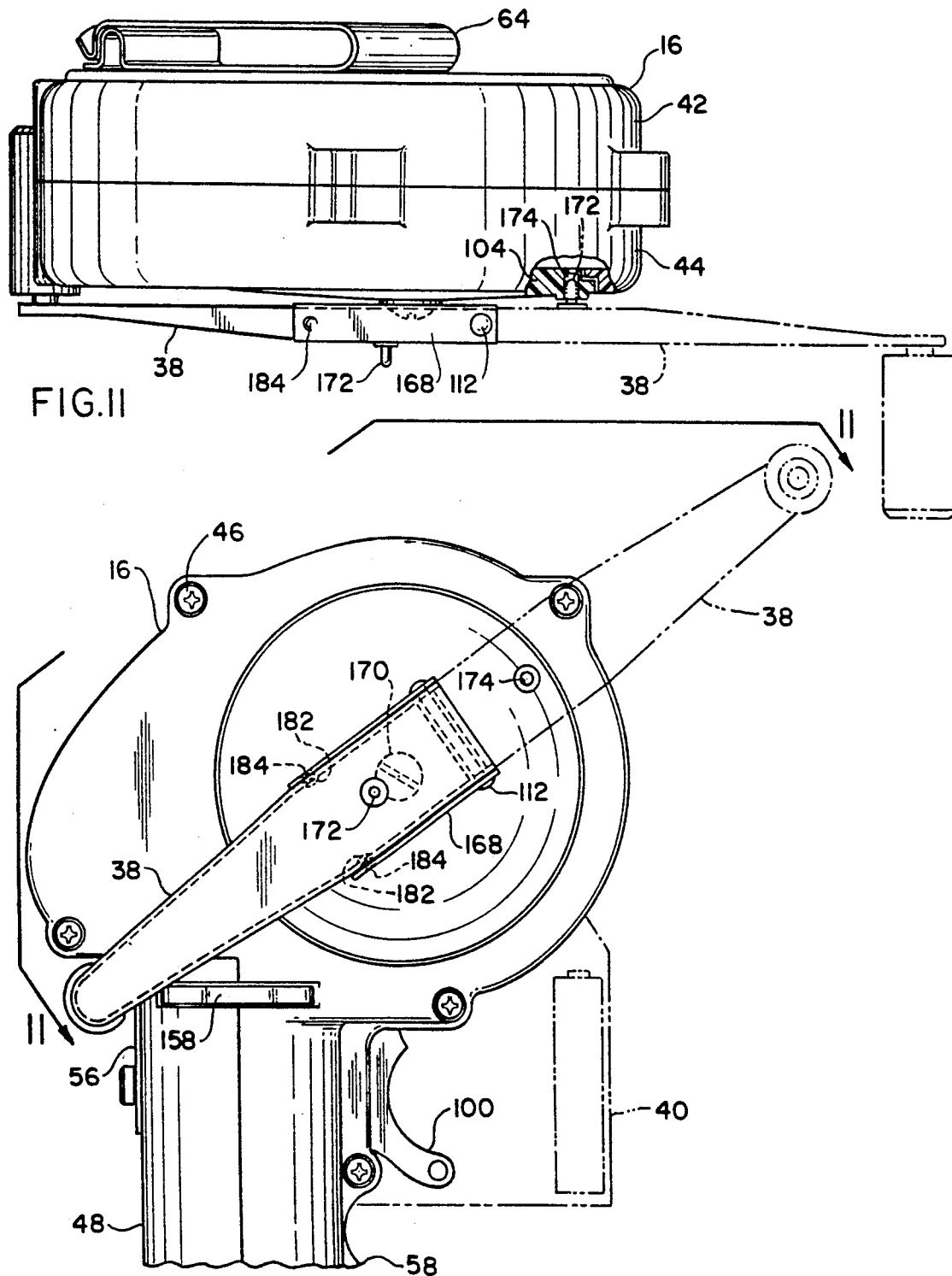
FIG. 11 is a plan view as taken along line 11—11 of FIG. 12 illustrating details in the crank mechanism used to uncoil the negator spring thereof.
FIG. 12 is a partial right side elevational view projected from FIG. 11.

The assembled IV pump 10 is now ready to be placed in the condition necessary for use, wherein in effect it undergoes a "wind up". More particularly, as best seen in FIGS. 11 and 12, crank 38 is unfolded from its storage full line position about hinge 112 and moved into its phantom perspective position in which pin 172 aligns with grip hole 174 in face plate 104. In this unfolding movement detents 182 in the crank arm 38 release from cooperating depressions 184 in hinge plate 168. The user maintaining one hand on the pistol grip 58 turns crank 38 clockwise approximately 210 degrees until the interconnected spheres 82 or syringe powering means 30 is prevented from further movement by a stop (not shown). As a result of this clockwise rotation, the syringe powering means 30 is in its ready position wherein the negator spring 28 is fully extended as shown in FIG. 8. Pawl 132 will retain spindle 68 against rotation under the holding action of ratchet wheel 98, and this condition will remain until trigger 100 is compressed or actuated.

This is a procedure which can be performed manually by the patient or by an attendant. The actual process of achieving intravenous feeding is well understood, and need not be described for an understanding of the invention. It is significant to note, however, and again with reference to FIG. 1, that the intravenous pump 10 is of an optimum noteworthy compact size in which it is readily supported on the waist belt 14 of a patient 12. It is also readily convenient to use. More particularly, as may be readily understood from FIG. 8, trigger 100 is adapted to be squeezed clockwise, which results in pawl parts 134 and 136 also moving clockwise. As a consequence, catch hook 140 moves upward and release hook 142 moves downward. In the time interval in which this occurs, hook 96 releases ratchet wheel 98 and catch hook 140 is in position to engage a next-in-line tooth on the ratchet wheel 98. When trigger 100 reaches the clockwise extreme position of its cycle, ratchet wheel 98 and, of course, also spindle 68, will have moved one tooth space clockwise. Assuming the patient has released the trigger 100, this permits the release hook 96 to engage the next tooth on ratchet wheel 98 in a well understood manner. As a consequence, the trigger mechanism 34 allows the spindle 68 to advance counterclockwise the distance of one ratchet tooth space at a time, during which the interconnected spheres 82 are urged by the negator spring 28 into the syringe barrel 18 with a constant force which is characteristic of a negator spring. In the IV pump herein described, each one-tooth cycle of trigger 100 is adapted to deliver a 1 cc. volume of medicant 36 from the syringe 20.

An alternate operational mode of the IV pump 10 is to have a constant flow from the syringe 20. In this operational mode, pawl 132 is disengaged completely from ratchet wheel 98 by pressing knob 152 inwardly and advancing trigger 100 until pin 146 engages in hole 144 in pawl part 136. This arrangement allows spindle 68 to freely rotate counterclockwise about its rotational axis 66. During this operational mode when it is desired to nevertheless discontinue flow to the patient, all that is necessary is slight pressure on trigger 100 which will cause outwardly biased pin 146 to drop out of hole 144 and hook 96 to then engage the ratchet wheel 98.

While the IV pump or syringe having the noteworthy compact size as fully explained herein is fully capable of attaining the objects and providing the advantages hereinbefore stated, it is to be understood that it is merely illustrative of the presently preferred embodiment of the invention, and that no limitations are intended to the detail of construction or design herein shown other than as defined in the appended claims.

What is claimed is:

1. A negator spring-powered syringe having a compact sized non-linear compartment for said negator spring comprising a centrally disposed circular-shaped spindle having a peripheral surface for supporting movement therealong of a piston rod for said syringe, plural interconnected spheres serving as said piston rod disposed against said spindle support surface and extending therealong such that a distal positioned sphere is in a clearance position from said syringe and a proximal positioned sphere is in an adjacent position thereto, and a negator spring in an uncoiled configuration connected to extend from said proximal positioned sphere in encircling relation about said plural interconnected spheres into engaged relation with said distal positioned sphere, whereby during the coiling of said negator spring said connection to said distal positioned sphere urges said plural interconnected spheres in a circular path along said spindle support surface and into said syringe led by said proximal positioned sphere to thereby obviate the need of a linear oriented compartment for storing said interconnected spheres during non-use.

2. A negator spring-powered syringe as claimed in claim 1 wherein said circular-shaped spindle is V-shaped in cross section to facilitate the tracking of said interconnected spheres in the included angle of said V-shape.

3. A negator spring-powered syringe as claimed in claim 2 wherein said sphere encircling negator spring is in contact both against and also lengthwise of said interconnected spheres, whereby the urgency of said negator spring is in lengthwise relation to said interconnected spheres to urge said interconnected spheres through a power stroke and also in radial relation to said interconnected spheres to hold said interconnected spheres in said included angle of said V-shape of said spindle to maintain the proper tracking thereof.

4. A negator spring-powered syringe as claimed in claim 3 including a crank operatively connected to rotate said spindle in a direction opposite to the directional movement of the interconnected spheres under the urgency of said negator spring, whereby rotation of said crank is adapted to return said interconnected spheres to a starting position of movement preparatory to the power stroke thereof.

* * * * *